(12) United States Patent
Becker et al.

(10) Patent No.: US 12,061,162 B2
(45) Date of Patent: Aug. 13, 2024

(54) APPARATUS AND METHOD FOR DETECTING TRACE METALS WITH ELECTRICALLY CONDUCTIVE DIAMOND ELECTRODES

(71) Applicant: Fraunhofer USA, Inc., Plymouth, MI (US)

(72) Inventors: Michael Frank Becker, East Lansing, MI (US); Thomas Schuelke, Pinckney, MI (US)

(73) Assignee: FRAUNHOFER USA, INC., Plymouth, MI (US)

( * ) Notice: Subject to any disclaimer, the term of this patent is extended or adjusted under 35 U.S.C. 154(b) by 0 days.

(21) Appl. No.: 17/381,173

(22) Filed: Jul. 20, 2021

(65) Prior Publication Data
US 2021/0349047 A1 Nov. 11, 2021

Related U.S. Application Data

(62) Division of application No. 15/751,133, filed as application No. PCT/US2016/046063 on Aug. 8, 2016, now Pat. No. 11,073,494.

(51) Int. Cl.
| | | |
|---|---|---|
| *G01N 27/30* | (2006.01) | |
| *B01L 3/00* | (2006.01) | |
| *C02F 1/461* | (2023.01) | |
| *C02F 1/467* | (2023.01) | |
| *G01N 27/42* | (2006.01) | |
| *G01N 33/18* | (2006.01) | |

(52) U.S. Cl.
CPC ...... *G01N 27/308* (2013.01); *B01L 3/502707* (2013.01); *B01L 3/502715* (2013.01); *C02F 1/46109* (2013.01); *C02F 1/467* (2013.01); *G01N 27/302* (2013.01); *G01N 27/42* (2013.01); *B01L 2300/0645* (2013.01); *B01L 2300/087* (2013.01); *C02F 2001/46147* (2013.01); *G01N 33/1813* (2013.01)

(58) Field of Classification Search
CPC .... G01N 27/308; G01N 27/302; G01N 27/42; G01N 33/20; B01L 3/502707; B01L 3/502715; B01L 2300/0645; C02F 1/46109; C02F 1/467; C02F 2001/46147
See application file for complete search history.

(56) References Cited

U.S. PATENT DOCUMENTS

2014/0069811 A1 * 3/2014 Newton ............ G01N 27/4163
204/406

FOREIGN PATENT DOCUMENTS

JP 2014232052 A 12/2014

OTHER PUBLICATIONS

Smirnov et al., "Integrated All-Diamond Ultramicroelectrode Arrays: Optimization of Faradaic and Capacitive Currents," Anal. Chem. 2011, 83, 7438-7443 (Year: 2011).*
Hynek et al., "Automated Voltammetric Determination of Lead(II) Ions Using Sensor Array," Int. J. Electrochem. Sci., 8 (2013) 4441-4456 (Year: 2013).*

(Continued)

*Primary Examiner* — Alexander S Noguerola
(74) *Attorney, Agent, or Firm* — Craig A. Phillips; Dickinson Wright PLLC

(57) ABSTRACT

A trace metal analysis detector and method of operating the same to detect metals in various fluid samples using boron doped diamond working electrodes.

11 Claims, 11 Drawing Sheets

(56) References Cited

OTHER PUBLICATIONS

Peterson et al., "Fundamentals of stripping voltammetry," American Laboratory, Nov. 1981, Princeton Applied Research—Electrochemistry Product Group Application Note S-6 (Year: 1981).*

McGaw McGaw et al., "Diamond Thin-Film Electrodes for Monitoring Heavy Metal Ions in Water Supplies Using Anodic Stripping Voltammetry," SAE Transactions, vol. 114, Section 1; Journal of Aerospace (2005), pp. 293-299 (Year: 2005).*

Ming Li et al. "Nanostructured Sensors for Detection of Heavy Metals: A Review." ACS Publications, ACS Sustainable Chem. Eng. 2013, 1, 713-723, 11 Pages.

\* cited by examiner

APPARATUS AND METHOD FOR DETECTING TRACE METALS WITH ELECTRICALLY CONDUCTIVE DIAMOND ELECTRODES

CROSS-REFERENCE TO RELATED APPLICATIONS

This application is a divisional of application Ser. No. 15/751,133 filed on Feb. 7, 2018, which is a 371 of International Application No. PCT/US2016/046063 filed on Aug. 8, 2016, which claims the benefit of U.S. Provisional Application Ser. No. 62/202,422 filed Aug. 7, 2015, which are incorporated herein in their entireties.

BACKGROUND OF THE INVENTION

1. Field of the Invention

The present invention is directed to a trace metal analysis detector including electrically conductive diamond material configured to detect metals in various samples. The present invention provides an apparatus and method that allows accurate, precise and repeatable detection of trace metals that are very difficult to detect with traditional electrodes used in anodic and cathodic stripping voltammetry and also an improvement in sensitivity for detecting difficult to detect analytes with traditional detectors, including the use of doped diamond electrodes, specifically electrodes including a thin film of boron doped diamond material.

2. Description of the Prior Art

A number of apparatuses and methods exist for detecting specific analytes in a sample. Common samples include ground water, food analysis, industrial discharge, product samples, drinking water, and any sample where it is desirable to detect specific analytes using an electrode in anodic or cathodic stripping voltammetry. More specifically, anodic and cathodic stripping voltammetry have been used for quantitative determination of specific ionic species by electroplating or depositing one or more analytes on a working electrode during a deposition step, and in some instances oxidizing or removing the analyte from the electrode during a stripping step. More specifically, the current is measured during the stripping step, specifically during anodic stripping voltammetry, the oxidation of species registers as a peak in the current signal from the electrode, i.e. the potential at which the ionic species begins to be oxidized.

Traditionally, detector systems use three electrodes, a working electrode, an auxiliary or counter electrode and a reference electrode. Historically, the working electrode is formed of a bismuth or mercury film electrode (in a disk or planar strip configuration). The mercury film forms an amalgam with the ionic analyte of interest, which upon oxidation results in a sharp measurable peak. Because certain analytes of interest have an oxidizing potential above that of mercury, or where a mercury electrode would be otherwise unsuitable, and in view of the environmental issues with mercury, including toxicity, stability, and volatility issues, a solid, inert metal such as silver, gold, or platinum are more commonly used now in modern detectors. Even with solid metal electrodes (typically plated or thin film coated over a base or substrate), using a metal electrode also creates issues where the desired trace elements may overlay or not be able to be detected. For example, a metal electrode is not able to detect the same metal, from which it is formed, in the sample. Furthermore, metal electrodes have smaller potential windows, which limit the measurement of certain metals, and metal electrodes exhibit higher background current effects. Some alternate electrode materials include Ir, Bi, Au, Ag, and graphite. The deposition of a metal adlayer on bare solid electrodes is a more complicated process than in the case of forming an Hg amalgam (i.e., deposition of the metal within a volume of Hg). The activity of a deposit depends on the amount deposited, the interaction of the deposit with the electrode, and the distribution on the surface. The practical utility of any electrode depends on its effectiveness for detecting metal ions in "real world" samples, such as, water samples.

Recent developments have shown that doped diamond electrodes, such as boron-doped diamond (BDD) thin films, possess improved properties as compared to metal electrodes, including a wider electrochemical potential window, low and stable capacitive background current, high response reproducibility and long-term response stability. Boron doped diamond electrodes are also better suited for analyzing metals present in toxic solutions as they are generally inert and do not react with the sample or solution, unlike many metal based electrodes. Even in view of the benefits of boron doped diamond electrodes, they still include many issues. Currently, only the working electrode of the required three electrodes is formed from boron doped diamond in trace metal detectors. Instead, the reference electrode is typically made of a silver chloride while the counter electrode is made of a platinum material. To date, no system has been able to form the reference electrode, the counter electrode, or both the reference electrode and counter electrode out of a boron doped diamond material, while yet being able to provide consistent and accurate results.

In addition, current methods require that each working electrode be operated to deposit analytes, such as metal ions during a single deposition step and then measure the current during a single stripping step by doing a sweep of potential over time, as illustrated in FIG. 1. For example, in anodic stripping voltammetry by applying a negative potential to the electrode and holding it for a specified time period, as in the illustrated time periods labeled B and C in FIG. 1, the desired analytes are deposited on the working electrode. Then the potential, as illustrated in the time period labeled D in FIG. 1, is slowly increased from negative to positive, and the current variations measured during this stripping step determine the types of analytes or ionic species present in the sample. One problem is that certain metal ions have similar potentials, so a peak measured at a specific potential may include more than one metal ion. As such, certain metals ions are incapable of being separated and may interfere under this method with the measurement of certain metal ions. In addition, peak suppression, peak shifting, and peak broadening may occur due to the formation of intermetallic complexes with a metal electrode. For example, copper has a suppressing effect to cadmium and zinc.

SUMMARY OF THE INVENTION

The present invention is generally directed to a detector apparatus and method for detecting ionic species, such as metal ions or certain organic molecules in a sample. The detector is generally used in connection with anodic or cathodic stripping voltammetry to determine the amount of selected ionic species in a sample.

The detector of the present invention not only may include a conductive diamond electrode, such as a boron doped diamond electrode, as the working electrode, but may also include at least one of the counter electrode or reference electrode formed from conductive diamond material. As such, both of the counter and reference electrodes may be made out of a conductive doped diamond material, such as boron doped diamond electrode material. The conductive diamond electrodes of the present invention have the advantage of a wider electrochemical potential window and a lower background signal, which enables a wider range of detectable metals and a high sensitivity or capability of detecting lower metal concentrations. In addition, electrodes made from conductive diamond are environmentally friendly and electrochemically long-term stable. Once calibrated, the detector utilizes a specific algorithm calculating trace metal concentration, as low as parts per trillion (ppt) levels (<100 ppt) of at least 15 metal ions with anodic stripping voltammetry, including antimony, arsenic, bismuth, cadmium, copper, gallium, germanium, gold, indium, lead, mercury, silver, thallium, tin, and zinc. In comparison, CSV may analyze arsenic, chloride, bromide, iodide, selenium, sulfide, mercaptans, thiocyanate, and thio compounds.

The present invention uses at least boron doped diamond (BDD) as the working electrode, Ag/AgCl as the reference electrode and Pt as the counter electrode. As stated above, all three types of electrodes may be formed of boron doped diamond material. All electrodes are in contact with the solution where the current flows between the working and counter electrode and the potential is measured between the working and reference electrode.

Applying a suitable potential to the working electrode, analytes, such as metal ions, are electroplated onto the working electrode surface. Each metal ion has a specific potential at which it is electroplated or deposited, according to the electrochemical series and reference electrode utilized. Once the analyte, such as a metal is electroplated or deposited, a reverse potential scan also known as stripping, is carried out towards positive potentials to oxidize/release and quantify the metals.

The detector is composed of a single working diamond electrode or a plurality of working diamond electrodes having a wider electrochemical potential window and a lower background signal, which enables a wider range of detectable metals and a high sensitivity or capability of detecting lower metal concentrations.

In the method of the present invention, each of the working electrodes is run at a different potential to deposit the desired analyte on the working electrode. In one method, these different potentials are done at the same time, while in other methods of the present invention it is important that these be done in sequence, so that a sample, having multiple analytes with different potentials on an ASV chart, would separate different analytes onto different electrodes depending on their potentials. This would allow more accurate and precise measurements, and prevent multiple analytes on a particular electrode from leaving at the same time, giving incorrect readings, particularly at very low levels of analyte in a sample. Once all scans are performed, the trace metal concentrations are calculated based on the peaks obtained by each of the reverse scans.

In the present invention using multiple electrodes, a first electrode may be driven to a first level of potential, the second electrode may be driven to a second level of potential, which is more negative than the first level, and if additional electrodes are present, each one will be driven to a more negative level then the other electrodes. If a plurality of working electrodes are driven to different potentials after the cleaning step, if performed at the same time, a more negative electrode will collect some of the ions of the less negative electrode. As such, when stripping, reading the results from the less negative electrodes, allows one to better determine the metals for the more negative electrodes as one can determine what is coming off for ions that overlap or are close to overlapping with more certainty.

The present invention as a trace metal analysis detector may be implemented on a micro fluidic lab-on-a-chip setup where the working electrode consists of electrically conductive diamond. The idea of the various compartments, each having separate working electrodes is that in each compartment, the working electrodes extract or separate certain metals from other metals in the sample so that the metals are not interfering with one another. The number of compartments will depend on how many metals will need to be analyzed and how much the metals of interest influence each other. More specifically, by sequentially removing the metal ions from the sample, the number of metal ions on any particular working electrode are minimized, thereby providing a cleaner signal for each electrode during the stripping process. The benefits of the present invention allow wide electrochemical potential scanning with low background noise, and allows detection of metals otherwise not easily detectable and increased sensitivity for lead, copper and zinc ions.

In addition, the inventors have surprisingly found that not only may an apparatus of the present invention be used to test for trace metals, but it also may be used to disinfect water and provide water purification. More specifically, by applying a high positive potential the electrodes generate —OH radicals, which break down the organics and sanitize the water, and a boron doped diamond electrode creates more free radicals, specifically hydroxyl radicals.

BRIEF DESCRIPTION OF THE DRAWINGS

Other advantages of the present invention will be readily appreciated, as the same becomes better understood by reference to the following detailed description when considered in connection with the accompanying drawings wherein.

DETAILED DESCRIPTION

Figure 1:
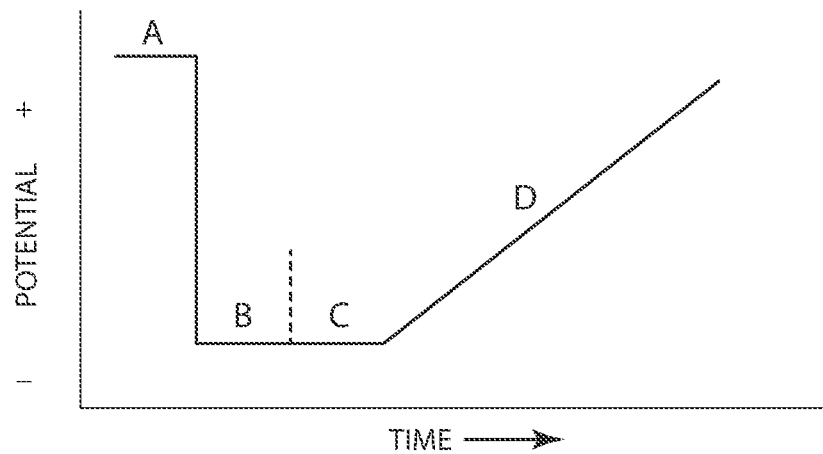
FIG. 1 is a graph of potential over time for traditional anodic stripping voltammetry.

The present invention is generally directed to a detector apparatus 10 and method for detecting ionic species, such as metal ions or certain organic molecules in a sample. The detector apparatus, 10 having a detector 20 and a controller 110 is generally used in connection with anodic or cathodic stripping voltammetry to determine the amount of selected ionic species in a sample. The detector 20 will primarily be described below and throughout the specification as being used in an anodic stripping voltammetry (ASV) method, however, it should be recognized that the detector 20 could easily be used with a cathodic stripping voltammetry (CSV) method instead with minor changes. Therefore, any reference to anodic stripping voltammetry may also be substituted with cathodic stripping voltammetry and changing swapping the positive and negative currents being applied at that time, as well as other minor changes.

The detector apparatus 10 may be formed in a variety of sizes, shapes and configuration, but generally includes a controller 110 in communication with three different types of electrodes 40, 50, and 60 as part of the detector 20. The types of electrodes used in the detector 20 include a working electrode 40, a reference electrode 50 and a counter electrode 60. In an ASV method, the working electrode 40 generally is used to deposit or preconcentrate the desired analytes onto its surface at negative potentials, and then selectively oxidize or strip the analytes, such as metals or other ionic species, from the surface 46 of the working electrode 40 during a potential sweep. The reference electrode 50 is used to ensure that the potential of the working electrode 40 is maintained properly, and minimizes the effects of the electrical field building up on the working electrode 40. More specifically, the reference electrode 50 is a stable potential and is the baseline measurement electrode potential, and its performance directly affects the heavy metal detection, stability, reproducibility, and accuracy. The counter electrode 60 measures the current flow, and provides the counter flow for the working electrode 40.

The detector 20 of the present invention not only includes a conductive diamond electrode, such as a boron doped diamond electrode, as the working electrode 40, but may also includes at least one of the counter electrode 60 or reference electrode 50 formed from conductive diamond material, or both of the counter electrode 60 and reference electrode 50 made out of a conductive doped diamond material, such as boron doped diamond electrode material. It should be recognized that when referring to a boron doped diamond electrode, the electrode could be but is generally not bulk boron doped diamond but generally a film or thin film of boron doped diamond material 44 laid over a base or substrate 42 to form the electrode. Over conventional designs that use mercury and bismuth electrodes, it has been found that conductive diamond electrodes have the advantage of a wider electrochemical potential window and a lower background signal, which enables a wider range of detectable metals and a high sensitivity or capability of detecting lower metal concentrations. In addition, electrodes made from conductive diamond are environmentally friendly and electrochemically long-term stable. No additional devices are needed as compared to fluorescent, surface plasmon resonance or surface enhanced Raman scattering sensors.

As stated above, the invention is a trace metal analysis detector apparatus 10 using electrically conductive diamond electrode material, as the electrodes. Once calibrated, the detector apparatus 10 utilizes a specific algorithm calculating trace metal concentration, as low as parts per trillion (ppt) levels (<100 ppt), as discussed below. The detector apparatus 10 of the present invention may analyze at least 15 metal ions with anodic stripping voltammetry, including antimony, arsenic, bismuth, cadmium, copper, gallium, germanium, gold, indium, lead, mercury, silver, thallium, tin, and zinc. In comparison, CSV may analyze arsemc, chloride, bromide, iodide, selenium, sulfide, mercaptans, thiocyanate, and thio compounds. The detection method of the present invention generally employs the electrochemical technique of ASV with specific variations. Anodic stripping voltammetry and cathodic stripping voltammetry are sensitive electrochemical analysis techniques used to investigate trace level metal impurities m aqueous solutions, traditionally parts per million, however the present invention has been found to detect metals in the parts per trillion. Various flavors of ASV and CSV exist and have been used to quantify metals in water. It should be recognized that any reference to ASV and negative or positive may be flipped for use in CSV.

The ASV technique employs, as do most electrochemical techniques, the three-electrode cell setup. The three electrodes 40, 50, and 60, as indicated above, are the working electrode 40, reference electrode 50, and counter electrode 60. The present invention uses at least boron doped diamond (BDD) as the working electrode 40, and typically silver or silver chloride (Ag/AgCl) as the reference electrode 50 and platinum (Pt) as the counter electrode 60. As stated above and discussed in more detail below, all three types of electrodes 40, 50, and 60 may be formed of boron doped diamond material. All electrodes 40, 50, and 60 are in contact with the solution where the current flows between the working electrode 40 and counter electrode 60 and the potential is measured between the working electrode 40 and reference electrode 50.

Figure 2:
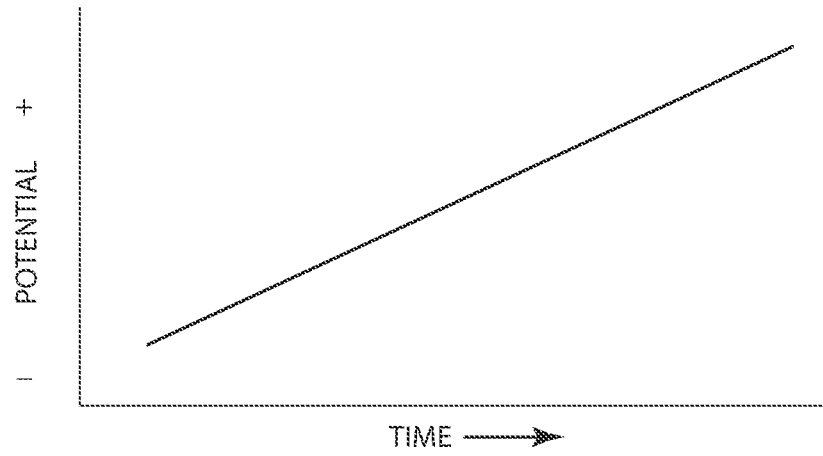
FIG. 2 is a graphical representation of a linear stripping method.
Figure 3:
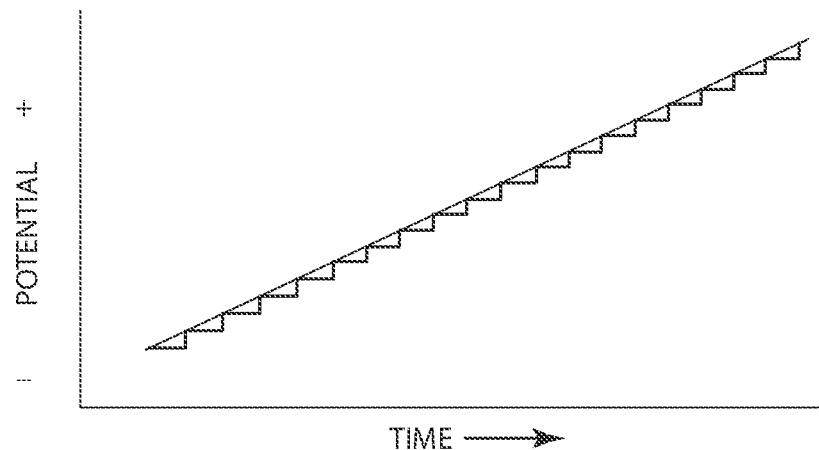
FIG. 3 is a graphical representation of a staircase linear stripping method.
Figure 4:
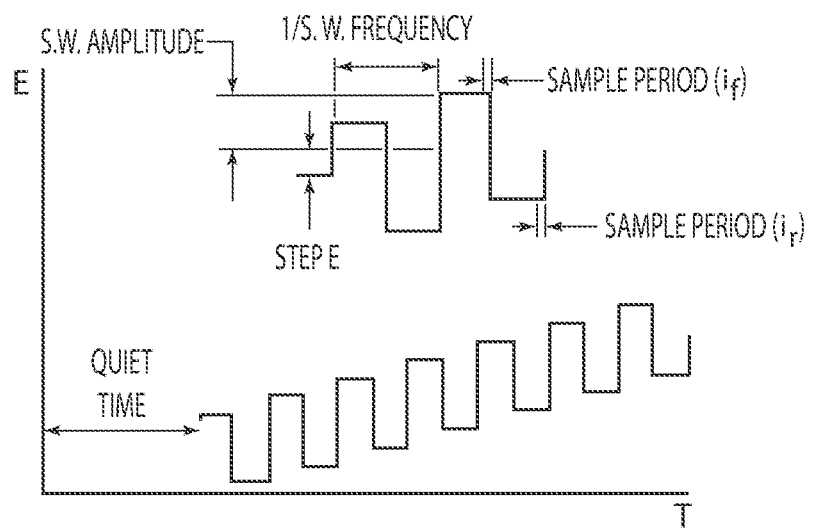
FIG. 4 is a graphical representation of a square wave stripping method.
Figure 5:
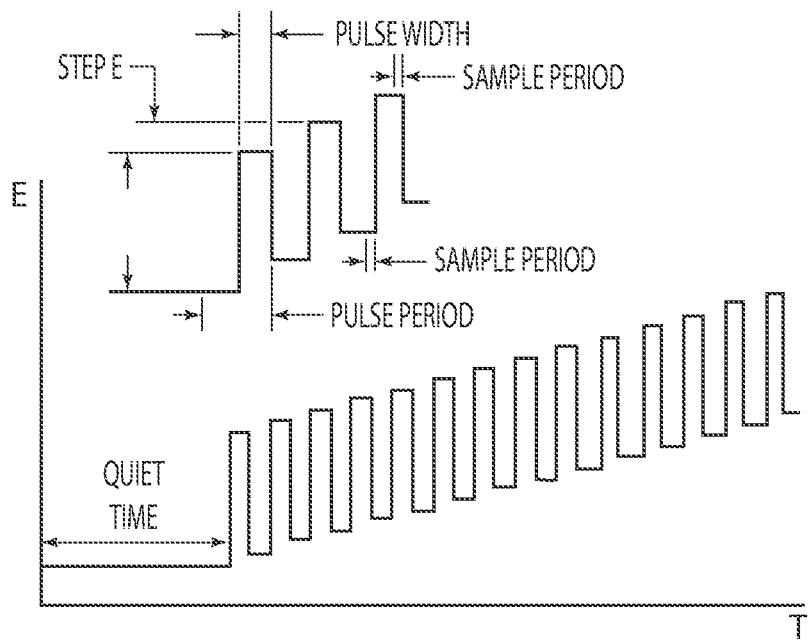
FIG. 5 is a graphical representation of a differential stripping method.
Figure 6:
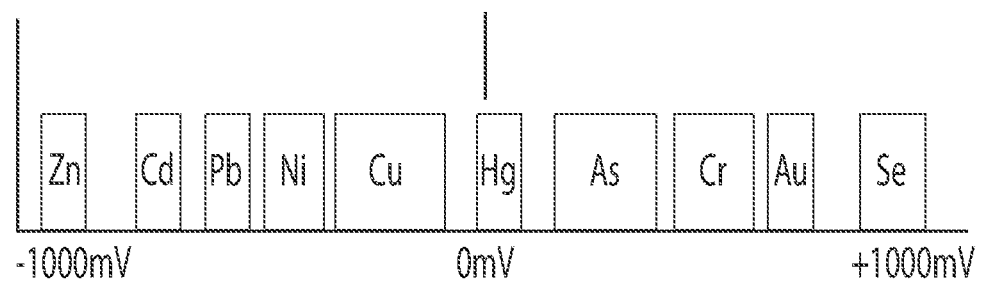
FIG. 6 is a graphical representation of the potential of metal ions.

Applying a suitable potential to the working electrode 40, analytes, such as metal ions, are electroplated onto the working electrode 40 surface. Each metal ion has a specific potential at which it is electroplated or deposited, according to the electrochemical series and reference electrode utilized, as illustrated in FIG. 6. From this plating potential, any potential slightly more negative will cause electroplating or deposition. Once the analyte, such as a metal is electroplated or deposited, a reverse potential scan also known as stripping, is carried out towards positive potentials to oxidize/release and quantify the metals. As described below, various ASV techniques depend on the reverse scan. The most common scans techniques are: (1) Linear voltammetry—LV, (2) Square wave voltammetry—SWV and (3) Differential pulse voltammetry—DPV. Once the scan is performed, the working electrode 40 will be held at a more positive potential to remove remaining metals and prepare the working electrode 40 for the next analysis. More specifically, current methods deposit all of the desired analytes on a single electrode and then run a potential sweep, which may be a linear, square wave or differential pulse sweep. There are some differences between Cathodic Stripping Voltammetry and Anodic Stripping Voltammetry, including that the potential sweeps are performed in the opposite directions, specifically negative to positive for Anodic Stripping Voltammetry, and positive to negative for Cathodic Stripping Voltammetry, but generally, the types of sweeps are identical and may be defined as one of linear, differential or square wave. A linear sweep, as illustrated in FIG. 2, generally means that the potential is changed in a linear fashion over time. More specifically, while the individual changes in potential may be in stepped fashion, they are generally infinitesimally small, such that the appearance of change over time is generally a line when graphically represented. FIG. 3 represents a variation of the linear sweep, known as a staircase sweep. In a differential pulse sweep, illustrated in FIG. 5, the step size, specifically the pulse amplitude or height, the pulse width and a rest width (if applicable) are all variable factors that can be adjusted to increase sensitivity. During the differential pulse sweep, the differential pulse wave form includes small pulses of constant amplitude superimposed upon the staircase wave form of a linear sweep, such that the current is sampled at two points during the pulse, one at the beginning of the pulse and one at the end of the pulse, and the difference between those two values is displaced or recorded. In square wave voltammetry, illustrated in FIG. 4, the potential wave form includes a square wave of constant amplitude superimposed on a staircase wave form. The current is measured at the end of each half-cycle and the current is measured on the reverse half-cycle and subtracted. The differential is displayed as a function of the applied potential and recorded as the data. It is important to note that in squarewave voltammetric analyses, the diffusion layer is not renewed between potential cycles. Thus, it is not possible/accurate to view each cycle in isolation; the conditions present for each cycle is a complex diffusion layer which has evolved through all prior potential cycles. The conditions for a particular cycle are also a function of electrode kinetics, along with other electrochemical considerations.

The detector 20 is composed of a single working diamond electrode 40 or a plurality of working diamond electrodes 40. Over conventional designs that use mercury and bismuth electrodes, it has been found that conductive diamond electrodes have the advantage of having a wider electrochemical potential window and a lower background signal, which enables a wider range of detectable metals and a high sensitivity or capability of detecting lower metal concentrations. In addition, electrodes made from conductive diamond are environmentally friendly and electrochemically long-term stable. No additional devices are needed compared to fluorescent, surface plasmon resonance or surface enhanced Raman scattering sensors.

In the method of the present invention, the working electrode 40 is run at a desirable potential to deposit the desired analyte on the working electrode 40. In systems using multiple working electrodes 40, each of the working electrodes 40 may be run at a different potential to deposit the desired analyte on the working electrode 40. In one method, these different potentials are done at the same time, while in other methods of the present invention it is important that these be done in sequence, so that a sample, having multiple analytes with different potentials on an ASV chart, would separate different analytes onto different electrodes depending on their potentials. This would allow more accurate and precise measurements, and prevent multiple analytes on a particular electrode from leaving at the same time, giving incorrect readings, particularly at very low levels of analyte in a sample. The difficulty of trace metal analysis is the potential interference between various metals present at the same time. For example, copper interferes with cadmium and zinc in a way that the presence of copper suppresses the cadmium and zinc peaks. With the utilization of separated scans on calibrated diamond working electrodes 40, it is possible to determine the individual metal concentrations more accurately.

Figure 7:
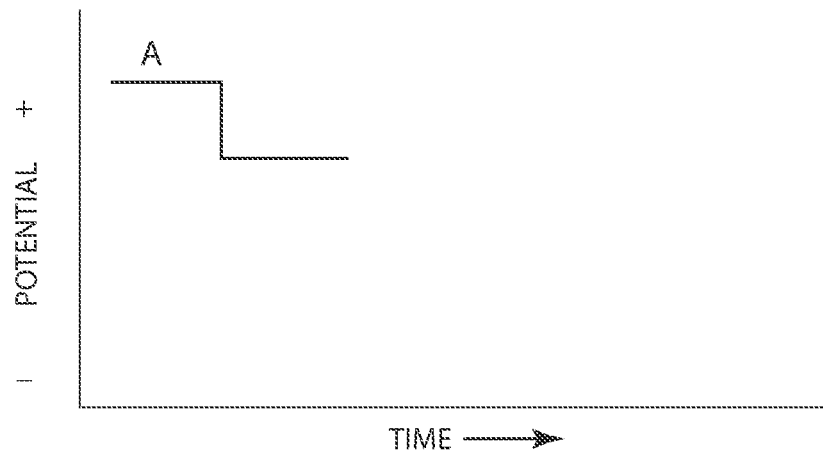
FIG. 7 is a graphical representation of the potential over time of the method of the present invention using a single working electrode.
Figure 8:
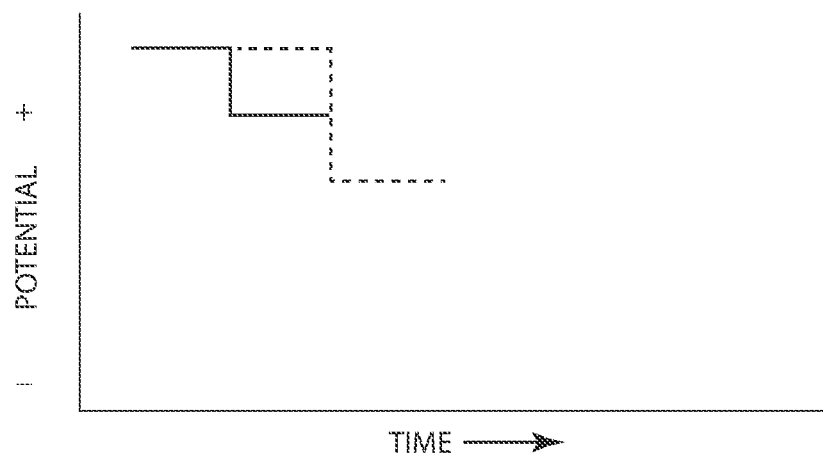
FIG. 8 is a graphical representation of the potential over time of the method of the present invention using three working electrodes.

More specifically, as provided in the ASV chart in FIGS. 6 and 7, the working electrode(s) 40 will be driven in anodic stripping voltammetry to a high positive potential to perform a cleaning step. During the cleaning step, any deposited materials that may give false positives will be driven off of the working electrode 40. As provided in FIGS. 6 and 7, the working electrode 40 is typically driven to the lowest negative potential during the method, immediately after the cleaning step. The following steps are then performed for the single working electrode 40 setup is as follows:

1) Hold a positive potential to condition/clean the working electrode 40 surface 46.
2) Apply a first predetermined electroplating potential to electroplate the first metal of interest (metal at the most positive plating potential).
3) Run a reverse scan (LV, SWV or DPV) on the working electrode 40 to a positive potential to quantify the first metal.
4) Hold a positive potential to condition/clean the working electrode 40 surface 46.
5) Apply a second predetermined electroplating potential, which is more negative than the first electroplating potential, to electroplate the first and second metal together on the working electrode 40.
6) Run a reverse scan (LV, SWV, or DPV) on the working electrode 40 to a positive potential to quantify the first and second metal together.
7) Hold a positive potential to condition/clean the working electrode 40 surface 46.
8) Apply a third predetermined electroplating potential, which is more negative than the first and second electroplating potentials, to electroplate the first, second and third metal together on the working electrode 40.
9) Run a reverse scan (LV, SWV, or DPV) on the working electrode 40 to a positive potential to quantify the first, second and third metal together.
10) Hold a positive potential to condition/clean the working electrode 40 surface 46.
11) Repeat the above steps for additional more negative electroplating potentials, as many times as desired, to plate and quantify additional desirable metals.

Once all scans are performed, the trace metal concentrations are calculated based on the peaks obtained by each of the reverse scans.

Figure 10:
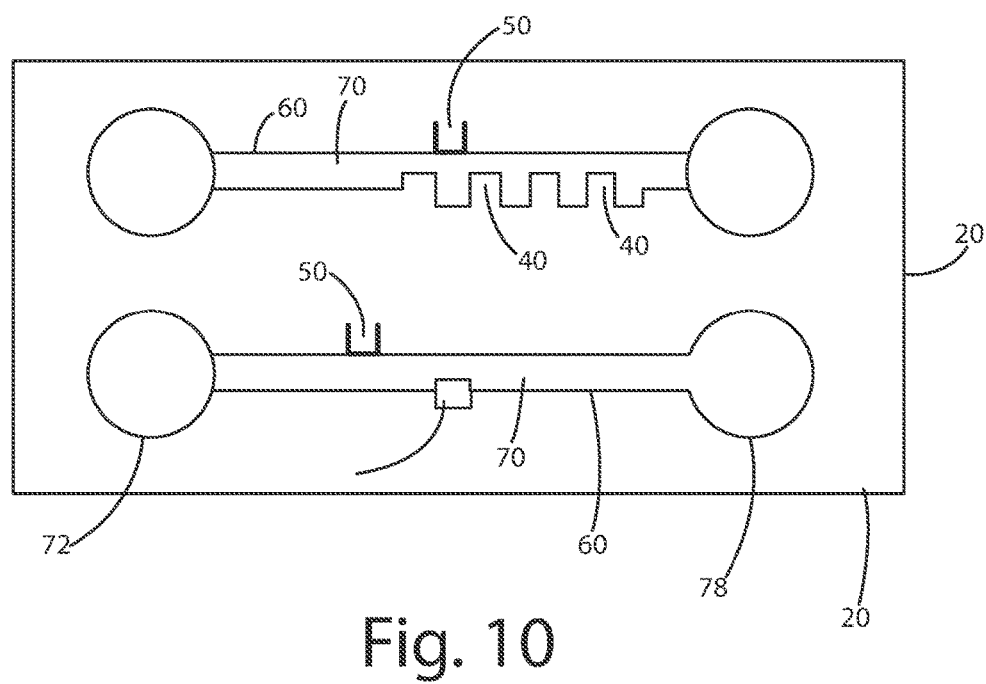
FIG. 10 is a perspective view of an exemplary system embodying the present invention.
Figure 22:
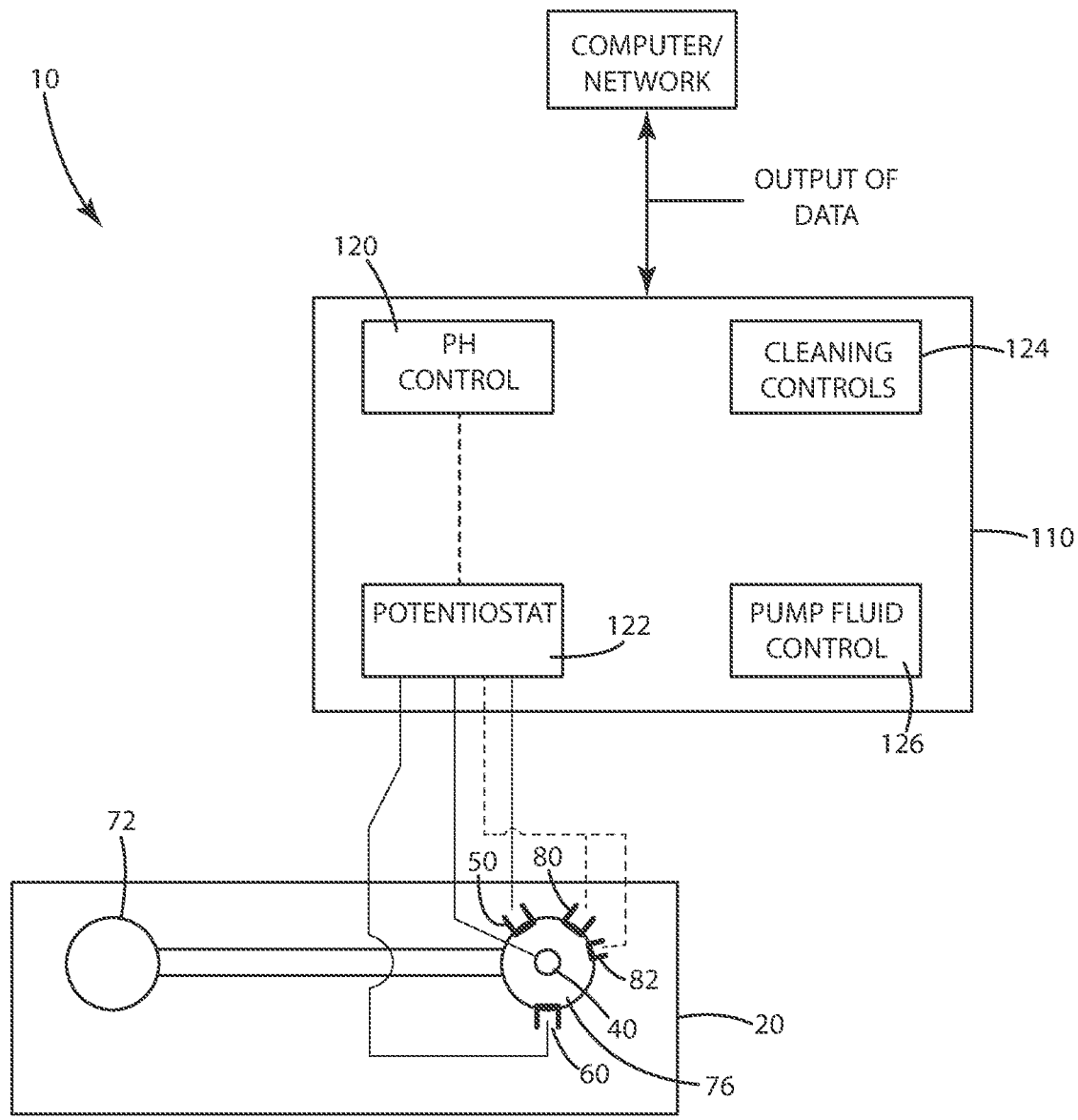
FIG. 22 is a schematic control diagram of the controller and the system.

The entire setup for the process described above may include a single sensor chip detector 20 with the three-electrode setup, as illustrated in FIG. 10, a miniature potentiometer including a readout unit to run the analysis, collect the data and transfer the data via a wire or wireless to a computer, smartphone or tablet, as schematically illustrated in FIG. 22. The working electrode 40 may consist either of a macro or micro electrode(s) which are the singular working electrodes 40, as illustrated in FIG. 10, or an array of conductive diamond, specifically boron doped diamond.

Figure 15:
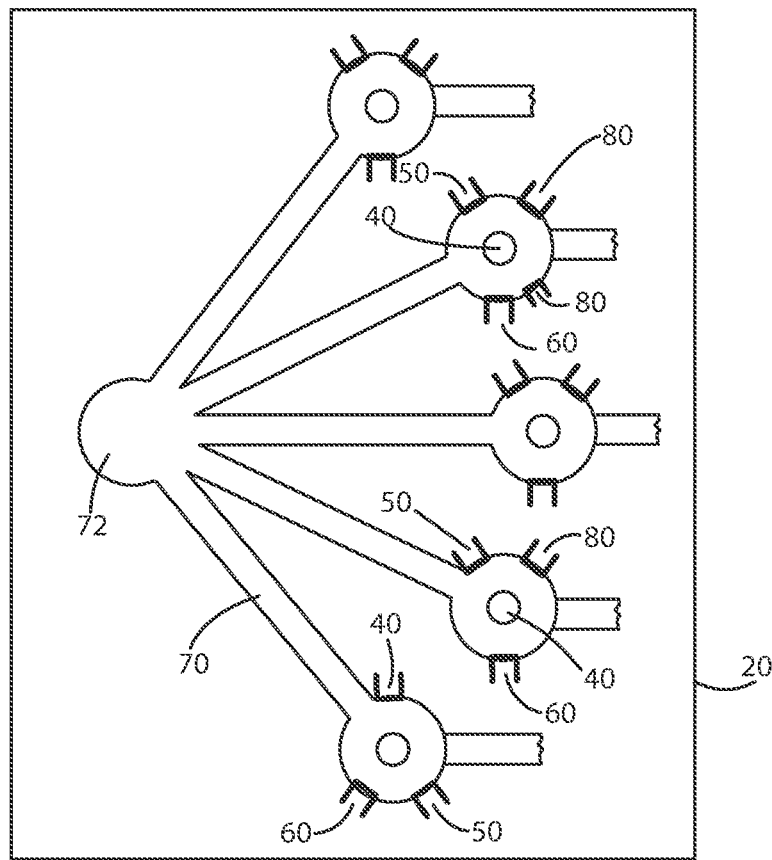
FIG. 15 is a perspective view of an exemplary system including parallel systems of the present invention.
Figure 17:
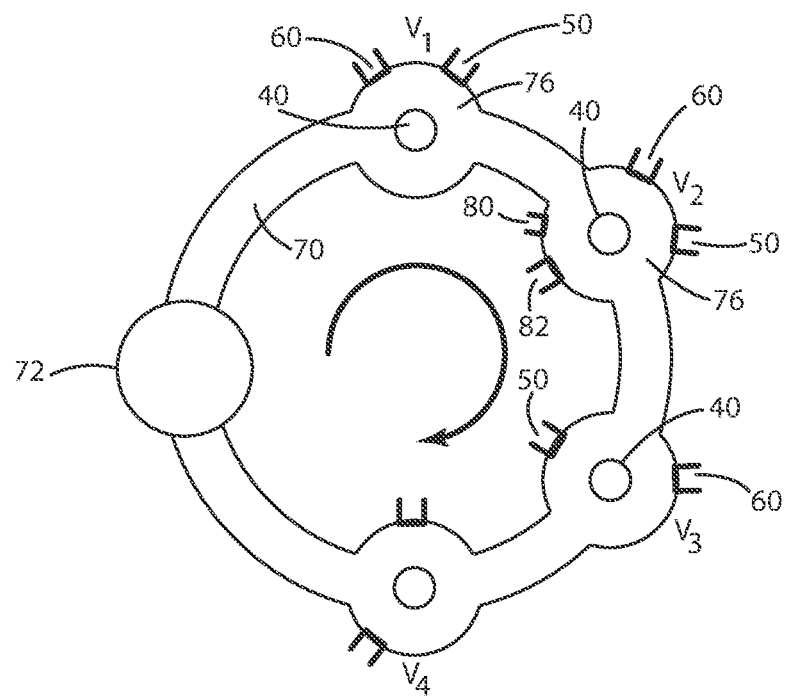
FIG. 17 is a perspective view of an exemplary system including serial systems of the present invention in a loop configuration.

The measurement principles for the multiple working electrode 40 setup, as illustrated in FIGS. 10, 15, and 17 is as follows:
1) Hold a positive potential to condition/clean all working electrode 40 surfaces 46 simultaneously;
2) Apply a predetermined electroplating potential to each working electrode 40, either simultaneously, in series with overlap, or in series spaced apart (or a variation thereof) to electroplate the metals of interest. Each working electrode 40 is held at a different potential depending on which metal will be analyzed in relation to that specific working electrode;
3) Run a reverse scan (L V, SWV or DPV) on each working electrode 40 to a positive potential to quantify the metals on each electrode 40, again simultaneously, in series with overlap, or in series spaced apart (or a variation thereof); and
4) Hold a positive potential to condition/clean all working electrode 40 surfaces 46 for the next measurement. The entire setup may include multiple sensor chips with the three-electrode setup, a multiplex potentiometer including a readout unit to run the analysis, collect the data and transfer the data via a wire or wireless to a computer, smartphone or tablet.

More specifically, in the present invention using multiple electrodes, a first electrode may be driven to a first level of potential, the second electrode may be driven to a second level of potential, which is more negative than the first level, and if additional electrodes are present, as illustrated in at least FIGS. 10, 15, and 17, each one may be driven to a more negative level then the other electrodes. As such, a first working electrode 40 may be driven to a first potential, while the remaining four electrodes 40 may equally split the whole potential, or be configured at potentials to each target a different metal. For example, FIG. 6 shows an anodic stripping voltammetry chart showing the relative placement of metal ions. From this chart, the first working electrode 40 could be driven to capture Selenium while a second working electrode 40 will be driven more negative, but still in the positive voltage range, will be configured to attract gold and chromium, while a third working electrode 40 is driven more negative than the other working electrodes, but still in the positive range, to attract arsenic and mercury. The next working electrode 40 may be actually driven into the negative to attract copper. Another working electrode 40 could then be driven more negative to attract nickel, lead and cadmium, and a final working electrode 40 be configured to be driven more negative to attract zinc. Of course, the above divisions are only exemplary, as well as the number of working electrodes. The method can be performed with only two working electrodes 40, or as many as practically desired, and the number of electrodes illustrated in the figures are only exemplary. While the working electrodes may also work at the same time, it also is capable of being performed in series, or series with some overlap, with some additional analysis benefits.

If a plurality of working electrodes are driven to different potentials after the cleaning step, if performed at the same time, a more negative electrode will collect some of the ions of the less negative electrode. Of course, this overlap in collection is less if the electrodes are arranged in series, such as illustrated in FIGS. 10 and 17, than the parallel tracks in FIG. 15. As such, when stripping, reading the results from the less negative electrodes, allows one to better determine the metals for the more negative electrodes as one can determine what is coming off for ions that overlap or are close to overlapping with more certainty. Furthermore, as described below, more analysis may be performed to provide improved results.

If a plurality of work electrodes 40 are driven to different potentials after the cleaning step and if they are performed in series, and then stripped simultaneously or in series, the electrodes may provide a more accurate reading. More specifically, the first electrode only attracts out the desired ions of analyte in the sample. As these would be the ones with the closest potential to the level used to clean the electrode, the ions that are attracted are the ones that would normally be attracted if another electrode was driven to a more negative potential. Therefore, by attracting out all of the first analyte, the second electrode with the next analytes will get a cleaner signal. The more electrodes used to separate out the analytes, the cleaner the signal. The series arrangement of electrodes in FIG. 16, may allow substantially all of the desired metal to be collected out of the liquid before it is moved into the next chamber for the next working electrode 40 to collect or capture the next desired metal, thereby giving highly accurate results with minimal adjustments to no adjustments for a working electrode capturing more than one metal.

The present invention as a trace metal analysis detector may be implemented on a micro fluidic lab-on-a-chip setup where the working electrode 40 consists of electrically conductive diamond. The calibrated detector utilizes a specific algorithm calculating trace metal concentrations of low parts per trillion (ppt) levels (<100 ppt). The detection method is employing the electrochemical technique of anodic stripping voltammetry (ASV) but could also be implemented for cathodic stripping voltammetry. The lab-on-a-chip setup includes an injection port or chamber 72, an optional micro pump 90, an optional pre-treatment compartment or chamber 74, at least one analysis compartment or chamber, channels or passageways 70 between chambers, optional acid, base or buffer solution compartments or chambers 102, additional volume chamber(s) 104, optional pH adjustment mechanisms 106 and dilution mechanisms 108 and an exit or end port or chamber 78. For ease of illustration on a number of figures the exit or end port, and the pump 90 is not illustrated, as some of the other chambers. In addition, any of the illustrated chips may include any of the above optional or other chambers in different configurations, and the illustrated configurations should not be considered limiting on what items of the present invention are included. The method of measurement of the lab-on-a-chip setup is as follows:

Depending on the sample, such as a water sample, a pretreatment step may be included to break up organic molecules in order to free up the desired analytes, such as organically bound metals. Without this step, only free metal ions will be detected, and the total amount of metal analyte in the sample would be incorrect. The pretreatment step may be performed on an electrically conductive diamond electrode, including the working electrode, but also can occur on an electrode in a pretreatment area or chamber 74, which includes an electrode but is not the working electrode. The pretreatment electrode may also be a pH adjustment electrode 80 or any other electrode and may be formed of any material, although it has been found that boron doped diamond works well for long life and efficient use as the pretreatment electrode. During operation, the pretreatment electrode, such as the pH electrode 80, is generally held at a potential high enough to generate hydroxyl radicals near the pretreatment electrode 80 surface capable of oxidizing organic molecules. After this pretreatment step, the pretreatment sample is pumped through the channels 70 to an analysis chamber 76, which includes the working electrode 40 for analysis.

In configurations without a pretreatment electrode, the pretreatment step can also occur during a cleaning step of the working electrodes 40. Prior to each measurement the working electrodes may be held at a positive potential to condition/clean the electrodes 40 for analysis as described above. J\tiore specifically, the water sample of interest is inserted into the inlet port or chamber 72 and pumped to the first reaction or analysis compartment 76. Here the sample volume is exposed to a high enough anodic potential to oxidize organic matter as part of the cleaning step thereby combining the cleaning and pretreatment steps. Of course, a pretreatment step may or may not be needed depending on the purity of the water sample. For highly contaminated water samples this step is necessary to avoid the influence of organic matter (i.e. binding metals such as Hg) falsifying the result. This will allow the method to determine the total metal content present versus the "free" metal content when some of the metal is bound to organic matter.

If a pretreatment step is used, the micro pump 90 then pumps the volume from the pretreatment compartment 74 to the second compartment, which may be an analysis compartment 76, including a working electrode 40. It should be noted that the pump may pump the volume to an additional or supplemental volume chamber 100, or other chamber as desired In the next compartment or chamber that is an analysis chamber 76 (first working electrode 40) the sample volume is exposed to a potential suitable electroplating more positive metals such as Ag and Cu. It should be noted that if the pretreatment and cleaning steps are combined, the first chamber electrode that performed the pretreatment step would also be the first working electrode 40. After the first metals are electroplated the micro pump 90 pumps the sample volume to the third compartment. In the third compartment or second analysis compartment 76 in this process (second working electrode 40), the sample volume is exposed to a greater negative potential than the prior working electrode used, which would be for example potential suitable for electroplating more negative metals such as Pb. After the second metal or set of metals is electroplated to the second working electrode 40 the micro pump 90 pumps the remaining sample volume to the fourth compartment. In the fourth compartment, the third analysis chamber 76 in this exemplary process (third working electrode 40), the sample volume is exposed to a potential suitable electroplating more negative metals such as Cd. The method could then continue, repeating the above steps. Once all compartments 74/76 are gone through, a reverse potential sweep is performed on each working electrode 40 to oxidize/release and quantify the metals. Each chamber is expected to include a reference electrode 50 and a counter electrode 60, although they could be placed between chambers in some embodiments. The electrodes 40, 50, and 60 are insulated from one another such that when sequential ASV is carried out, there is no interference between the electrodes 40, 50, and 60. Therefore, the potential of only a single electrode is measured, not across all electrodes.

The benefit of the various compartments, is that each analysis compartment 76 has separate working electrodes 40, allowing the working electrodes to extract or separate certain metals from other metals in the sample so that the metals are not interfering with one another. The number of compartments will generally depend on how many metals will need to be analyzed and how much the metals of interest influence each other. However, a chip having additional more compartments than the number of metals to be analyzed may always be used. More specifically, by sequentially removing the metal ions from the sample, the number of metal ions on any particular working electrode 40 are minimized, thereby providing a cleaner signal for each working electrode 40 during the stripping process. The benefits of the present invention allow wide electrochemical potential scanning with low background noise, and allows detection of metals otherwise not easily detectible and increased sensitivity for lead, copper and zinc ions. In addition, the lab on a chip allows controlled quantities to be dispensed into microfluidic arrays or chambers 76. The lab on the chip allows to implement chemical analytical algorithms for testing and the sequence of microfluidic chambers allowing for series removal of chemicals and ions out of the liquid sample, which increases the sensitivity of each following chamber 76 and working electrode 40 in the system 10.

In addition, the apparatus and method of the present invention also can change the pH of the sample without interfering with trace analysis of the various metals in the sample. More specifically, the pH may be changed through three methods. First, the pH may be changed to be more basic by running an electrode at a high positive potential for a period of time. Second, the pH may be changed to be more acidic through the electrode potential by running it at a high negative potential, but as this typically interferes with the metal analysis as it would plate metals to the electrode. The inventors have surprisingly found that a control burst that produces H+ ions that change the pH works, while yet providing a stable, accurate and repeatable analyte detection, such as trace metal detection as described above. For example, a potential sweep may be done on the sample as is, following the above described methods of the present invention. After this analysis is completed, the electrodes may provide a controlled burst to produce H+ ions that lower the pH and make the sample being analyzed more acidic, and then perform the sweep again to determine if the acidic nature of the sample frees up metal ions to provide a better read of the total metal ions, not just the free metal ions. More specifically, it may be important to determine the fraction of metal ions that are bound to organic matter and what metal ions are free in the environment, as well as the total metal ion content. In certain situations, knowing what is bound and not freely available may be important.

In the third method to adjust the pH, as part of the method of the present invention, a method step of pretreatment to provide a reproducible surface may be used. For example, a concentrated 1 molar acid may be introduced to the apparatus to clean the surfaces to eliminate leftover trace analytes, specifically metal ions on the surface of the electrodes or proximate to the electrodes. An exemplary configuration is illustrated in FIG. 13, as including an acid reservoir 102, which may easily be a base reservoir as well. The acid may be not as concentrated as described above and the electrode 40 may be used to concentrate the acid as desired through a charge to get the electrode acid clean. As described above, the third method may even be used in connection with the second method where the acid is generally created with a high negative burst on at least one electrode. In addition, as illustrated in FIG. 12, a combination of the third and second methods may be used, where a separate pathway The method may also include a step of washing with standard water between, which may also occur after the above described acid wash. The working electrode 40 would be cleaned and cycled to high potentials, until no metal remains. A cleaning cycle with a high positive potential drives the metals off of the surface, after which the electrodes may be calibrated using metal free water. The water and/or acid provide a reproducible surface. In addition, the calibration steps may be built into the device, or at least on the chip for the lab on a chip designs. This built-in cleaning step gives a reproducible surface, and that reproducible surface may have value built into the chip for each electrode 40 or be provided with each electrode 40 as the default surface, which eliminates manually calibrating the electrodes each time. In other words, the inventors have surprising found that the manufacturer can form the electrode and calibrate it, and provide the calibration information to the customer, and that the calibration stays relatively stable over time, unlike the prior silver or silver chloride electrodes. Then the customer may clean, test, clean, test in a repeatable fashion, without further calibration and use the provided values to save time. By having the working electrode 40 perform a pretreatment step, or using an acid chamber 102 to wash the electrode 40, it creates a reproducible surface that matches the calibrated surface. Running a scan in water before the sample will detect any metals present and will inform the user to clean further to ride the electrode surface of any metals, thereby ensuring that before a scan is started; no metals remain on the electrode. As such, being clean of metals would return the electrode to the preknown calibration, and the cleaning steps described herein allow the electrode to return to the calibrated state. One process the system may be configured to use is a step of cleaning, followed by a test step scan for metals, if metals are present, clean again, and test scan for metals, repeating until the metals fall below a threshold or are not measurable. If the cleaning with water fails to work, and acid wash may be performed, either through the electrodes or through the addition of acid.

Figure 9:
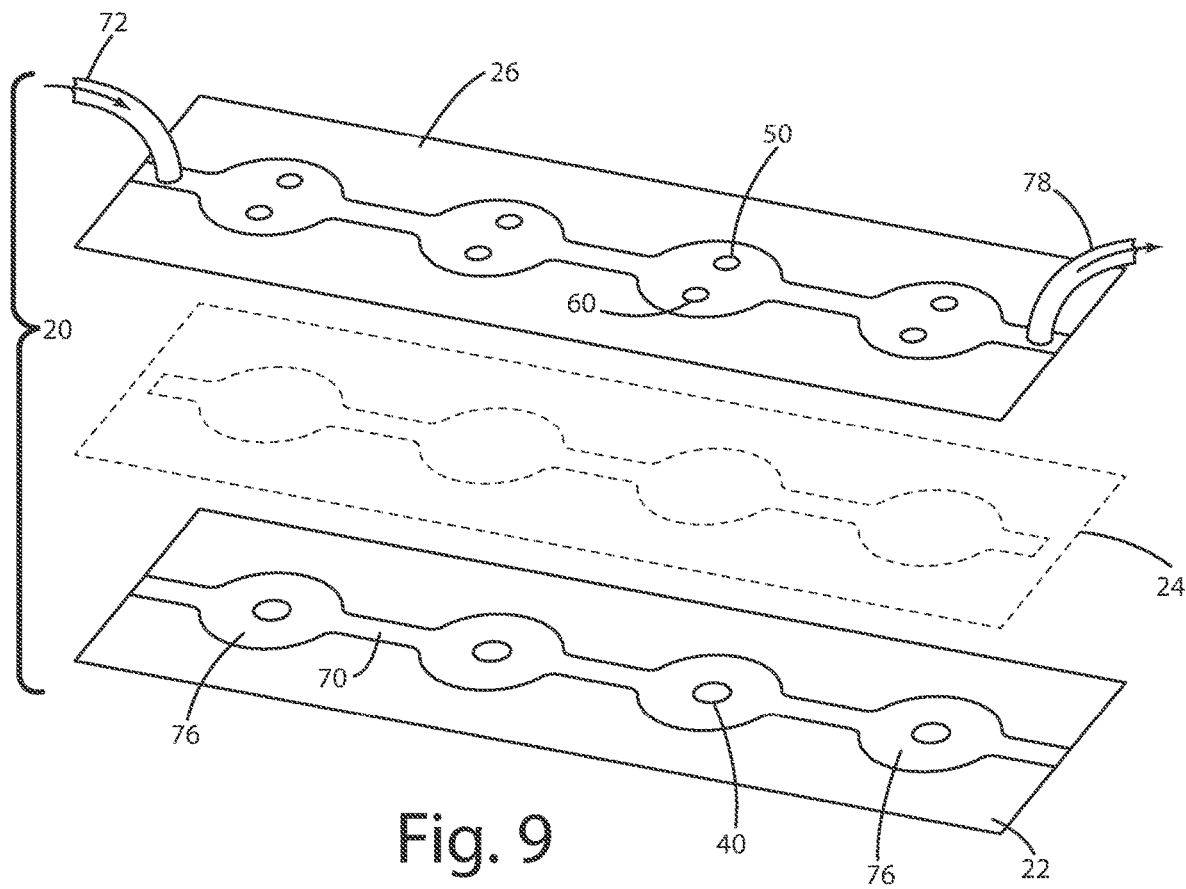
FIG. 9 is an exploded perspective view of an exemplary system embodying the present invention.

The maximize the ability of the electrode 40 to be cleaned and therefore be as close to the calibrated values for the electrode as possible, the chamber with the working electrode, including in the lab on a chip design may include a pH meter 82 to ensure the proper cleaning cycles. The apparatus with a pH meter 82 is very useful in samples that are dirty, include organic matter and the like when testing for trace metals, such as river water or ground water. To break down the organic matter, and clean the sample before testing, the pH meter 82 allows confirmation of the acid levels and acidic solution to ensure repeatable results, because differences in pH levels for certain solutions may provide different results in a trace metal analysis. The pH meter 82 when the working electrode 40 is cleaned at a high positive potential will look for a change in pH to ensure that the electrodes 40 and electronics are functioning properly to provide the expected change in ph. In addition, the present invention, as illustrated in FIGS. 9, 15 may have multiple tracks or paths, such that the system may use a parallel track system, as illustrated in FIG. 15, to create and prepare liquids in parallel, which with an additional mechanism for adjusting pH as described above allows for use of different tracks at different pHs. It should be noted that any of the pH adjustment mechanism, may be multiplied into parallel tracks. The different pHs may allow for quick analysis simultaneously of different pH levels, which allows for more accurate results that may be combined into a final result. More specifically, the first track may use the above described methods for cleaning and testing for trace metals in series, and the parallel track may use the electrode to change the pH and test in series as described above, and analyze the sample on as many other parallel tracks, at different pHs as desired. Then the system 10 may analyze and compare the results from the parallel channels, and use algorithms to determine with better sensitivity the desired analytes. Furthermore, the parallel tracks may also use the dilution mechanism 108 described below to dilute the sample and contrary to conventional wisdom to improve the sensitivity for the trace metals. Traditionally dilution reduced sensitivity and the prior art attempted to concentrate the samples. In addition, the dilution mechanism 108 may be used in a parallel track in combination with the acid or base modification 102 method above.

The apparatus or system when formed on a chip, such as illustrated in FIG. 9 may be easily formed out of a lower base material or substrate 22, including the electrodes 40, 50, and 60, a gasket or intermediate material 24 and a top material or cover 26 providing the sealed chambers 30.

The apparatus may also include a dilution mechanism 108 to dilute the sample, if desired. As described above, metals may be bound to or within organic matter, and the boron doped electrode (working electrode 40, pH electrode 80, or pretreatment electrode 75) may break down the organic materials and allow for better analysis, or the acid chamber 102, or other supplemental chambers 100 may be used. More specifically, the metals in organic materials may be shielded from detection as they are not available in the form of metal ions, and therefore using and acid or a base helps to break down the organic materials. As such, the system 10, such as the working electrode 40, pH electrode 80, if present, or a pretreatment electrode 75, if present, may be configured to produce either a high positive or high negative potential to change the pH of the sample. Of course, the pH may be changed through other mechanisms described above, such as the supplemental chambers 100, specifically acid or base chamber 102 as illustrated in FIG. 13 or a separate track including a pH adjustment electrode 80, such as illustrated in FIG. 12. For example, producing OH— or hydroxyl radicals help breakdown the organic materials and free up metal ions for detection. On advantage of the system is that it may self generate the radicals to make the solution acidic or basic. The pH electrode illustrated in FIG. 12 may not be in communication directly the input chamber 72 or reservoir of sample, but instead may have a separate injection port for a liquid such as water and then the system 10 may amend the pH with the pH electrode by injecting pH adjusted liquid into the analysis chamber 76. The electrode 40 is then followed by a cleaning step and the method may follow the steps listed above for cleaning and testing. The dilution mechanism 108 may also add any type of liquid that is helpful for analysis. It may be added during sample preparation or at each chamber.

In addition, the inventors have surprisingly found that not only may an apparatus of the present invention be used to test for trace metals, but it also may be used to disinfect water and provide water purification. More specifically, the electrodes may breakdown organics by applying a high positive potential, generating —OH radicals, which breakdown the organics, and sanitizes the water, and a boron doped diamond electrode has higher percent of free radicals, specifically hydroxyl radicals. In addition, the electrode 40 may then be driven to a negative potential to attract any heavy metals in the water, such that the water exiting the chamber is generally free of harmful pathogens and also free of undesirable heavy metals in drinking water. Of course, a water filter may be used to remove solids and organic matters and then the above method may be used to disinfect and kill any remaining pathogens and then remove any dissolved heavy metals. In addition, after such removal the apparatus may be used to detect metals.

The present invention may be used with a variety of samples, including water, blood, urine, and other aqueous samples. In addition, the present invention may also be used for chlorine detection as well as chlorine production. Lab on chip is good for heavy metal detection.

Figure 11:
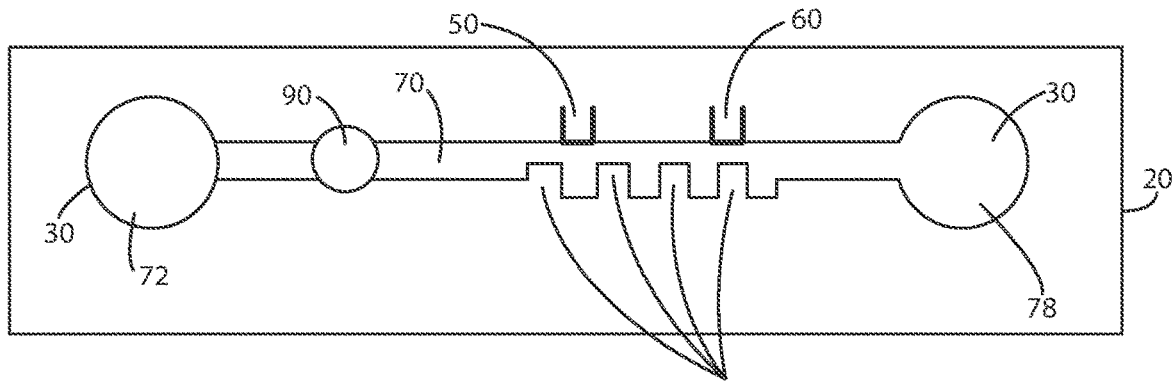
FIG. 11 is a perspective view of an exemplary system embodying the present invention.

Illustrated in FIG. 10 are two different systems for the present invention. One of the systems is first exemplary system using a single working electrode 40 in the passage 70 between the input chamber 72 and the exit port 78, and a second exemplary system having multiple working electrodes 40 in the passageway 70 between the input chamber 72 and exit chamber 78. The system also include a reference electrode 50 and counter electrode 60 in each of passageways 72. FIG. 11, also includes a micro-pump 90. While most of the figures are illustrated without the micro-pump, it should be understood that they are expected to be included even though they are not illustrated as some method of moving the sample between the inlet 72 and the analysis chambers is expected, although some chips may use a capillary action to move the sample, but relying solely on capillary action only allows small volumes of sample, is easily clogged by debris in the sample, and lacks control to do the steps precisely as desired and described above.

Figure 12A:
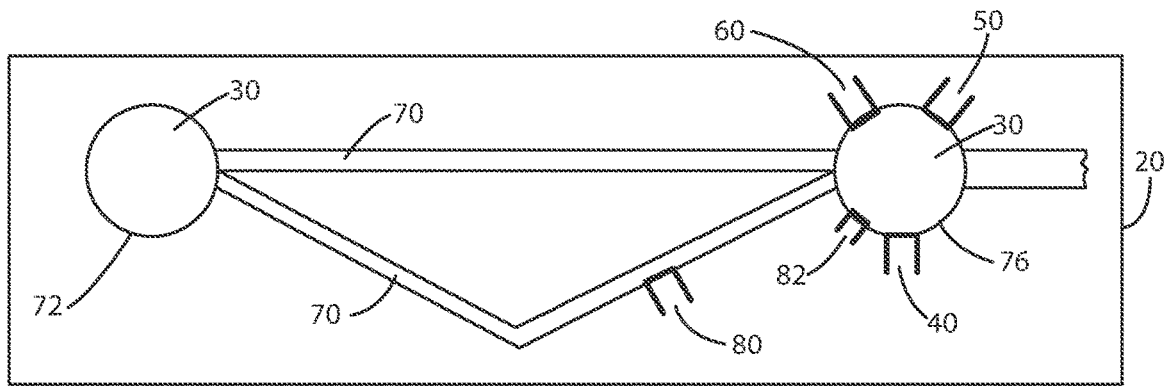
FIG. 12A is a perspective view of an exemplary system embodying the present invention and including a pH adjustment module.
Figure 12B:
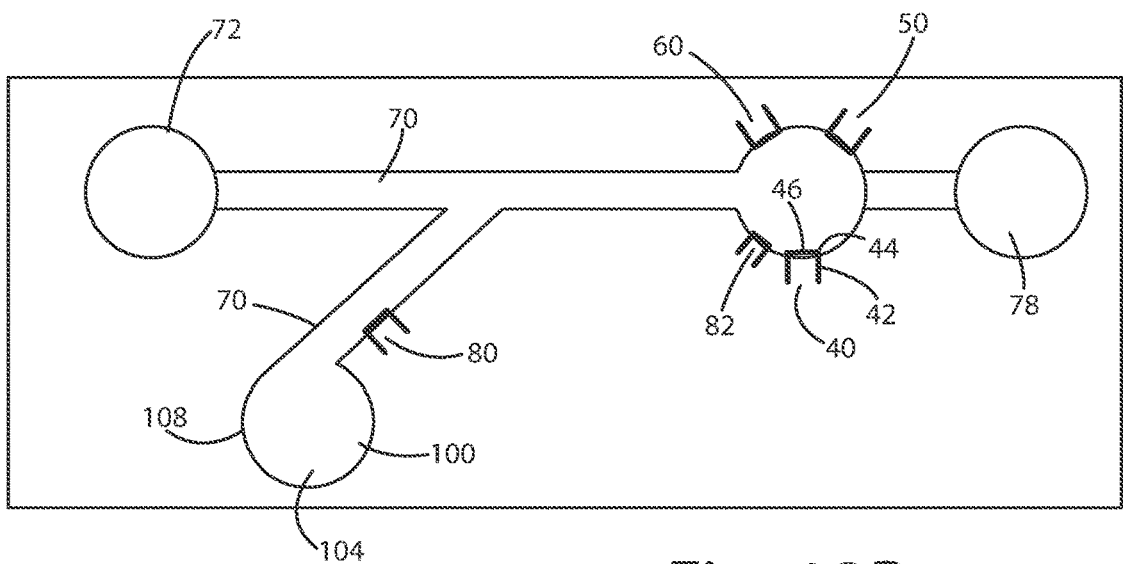
FIG. 12B is a perspective view of an exemplary system embodying the present invention and including a pH adjustment module.
Figure 13:
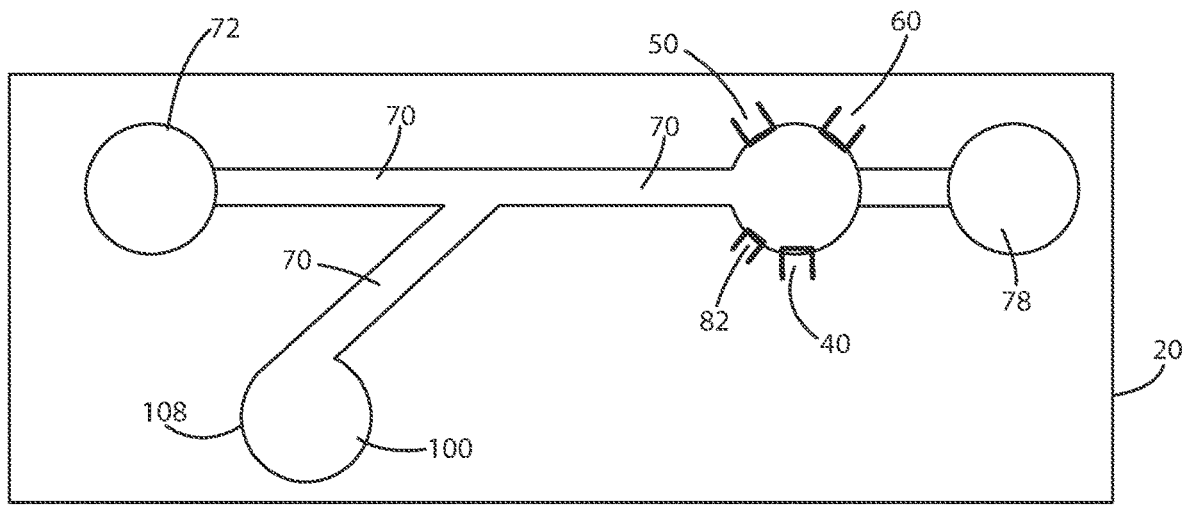
FIG. 13 is a perspective view of an exemplary system including an optional acid reservoir.

As illustrated in FIG. 12A, a separate pH electrode 80 may be included to adjust the pH, and uses a separate passageway to not affect the sample being analyzed if the pH electrode plates some metals while modifying the pH. As illustrated in FIG. 12B, the pH electrode may receive input from a second input or injection chamber 72, where a metal free liquid, such as distilled water may be injected, and then the system 10 uses the pH electrode to modify the pH of the liquid and inject it into the analysis chamber. A pH meter 82 may be included in the analysis chamber to monitor the pH. The advantage of this system is that the system can auto set or auto adjust the pH with minimal input from the user. The chamber 100 may also act as a dilution mechanism 108.

Figure 14:
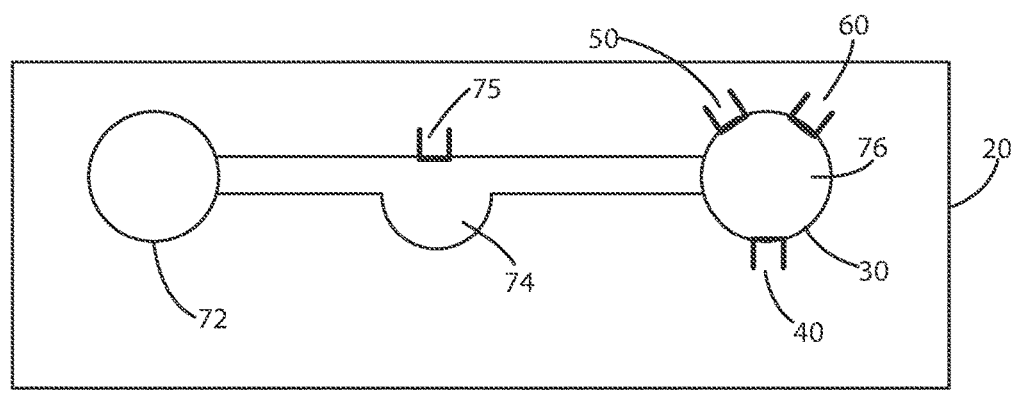
FIG. 14 is a perspective view of an exemplary system including a pH adjustment module.

As illustrated in FIG. 13, a supplemental chamber 100, such as an acid or base chamber 102 may be used. A micro-pump (not illustrated) may pump in an acid to the analysis chamber 70 as desired. A pH meter 82 may also be included in the analysis chamber 76. The system may pump in the acid or base as desired and if included, the pH meter can monitor and adjust how much is added to create the desired pH in the analysis chamber. While this system if fairly automatic, it requires the user to handle and acid or base as compared to FIGS. 12A and 12B. FIG. 14 includes a pH electrode 80 in the passageway 70 to adjust the sample pH as it is moved from the input chamber 72 to the analysis chamber 76. It is expected that a pH meter will also be included in the chamber 76.

A pretreatment chamber 74 is illustrated in FIG. 14, having a pretreatment electrode 75, which may be added to any of the exemplary systems or detectors. The pretreatment chamber 74 and electrode 75 may function as described above.

A detector chip having multiple parallel tracks is illustrated in FIG. 15. As illustrated, some may have optional pH electrodes and meters 80, 82, variations of working electrode configurations, all to accomplish the various functions described above. The illustrated detector is only illustrative and of course may be formed in other configurations, shapes and styles and include different functionality than shown. As described above, it has been found that the parallel method provides a much faster analysis, although the parallel method is much more data intensive.

Figure 16:
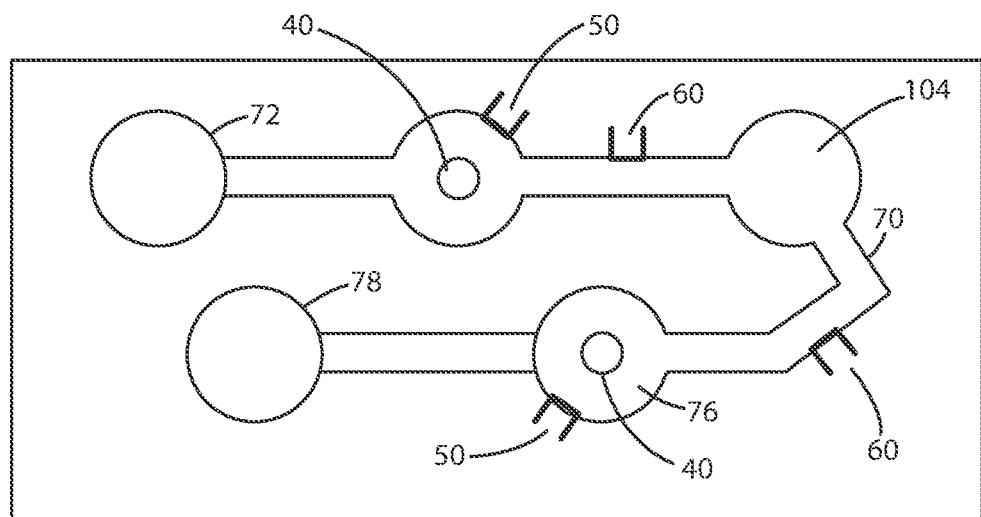
FIG. 16 is a perspective view of an exemplary system including serial systems of the present invention.

FIG. 16 shows a series of analysis chambers, and an additional volume chamber. The additional volume chamber allows for better metering into the analysis chambers of the samples. As many additional analysis chambers as desired may be added. It has been found that this serial method is more accurate than the parallel method in FIG. 15. FIG. 16 also illustrates an additional volume chamber to buffer the sample volume such that there is enough water or sample volume to pump to each new chamber. In addition, to avoid cross potential from the electrodes, it is recommended that the electrodes be spaced 2-3 times the effective range apart, but this may vary. Spacing the chambers further away also has the benefit of the passageways acting as a buffer amount of fluid, without the need for the additional volume chamber 104. These additional volume chambers 104 are also helpful in stopping the flow when stripping the metals. While some systems may have a constant flow to take off a metal such as copper and then later led, once there is enough volume in a chamber, it is expected that the flow will be stopped and then stripped of metals in the sample in the analysis chamber. Of course, as illustrated in FIGS. 10 and 11, the electrodes 40 are in the channel, so they may strip while in motion, and the counter electrode 60 may be the passageway 70 walls. In some processes, after enough time and flow, the copper is platted and then can apply anodic stripping and get a signal as the cupper is released. If only one analysis chamber 76 is available, then have to do it multiple times, but if multiple chambers, such as in FIG. 16 (which may have many more than two analysis chambers 76, the first chamber as described above stops and strips a first metal, closes to a neutral potential, the volume is then pumped to the next chamber free of the first metal. However to avoid contamination of the new sample communing in with the next analysis chamber, it may pump a portion of its fluid to the volume chamber 104 strip out, and then repeat to ensure no metals desired are let past the first analysis chamber to ensure accurate and precise measurements. In any event, the electrodes need to be configured to prevent interference and properly spaced far enough apart. Please note that the range of available metals, such as 10 ppm vs. 0.20 ppb may make the difference in the amount of required volume to pass by the sample to get an accurate reading.

A similar detector to the detector 20 in FIG. 16 is illustrated in FIG. 17. While it is cyclic in nature, it could also work in serial with a beginning and end point being different. It is expected that the detector in FIG. 17 would pump fluid to the first analysis chamber VI and then cycle that working electrode 40 on for s desired time period until all of the desired metal, such as copper is electroplated out. The volume is then pumped from the first to the second analysis chamber and then the electrode 40 in chamber v2 (76) is cycled on then off for the desired time until metal two is removed. Please note that chamber 1 could repeat the cycle at the same time for the first metal, or may stay off. If repeated, it would provide a cleaner sample to chamber two. The process is than repeated for v3 and then for v4.

Figure 18:
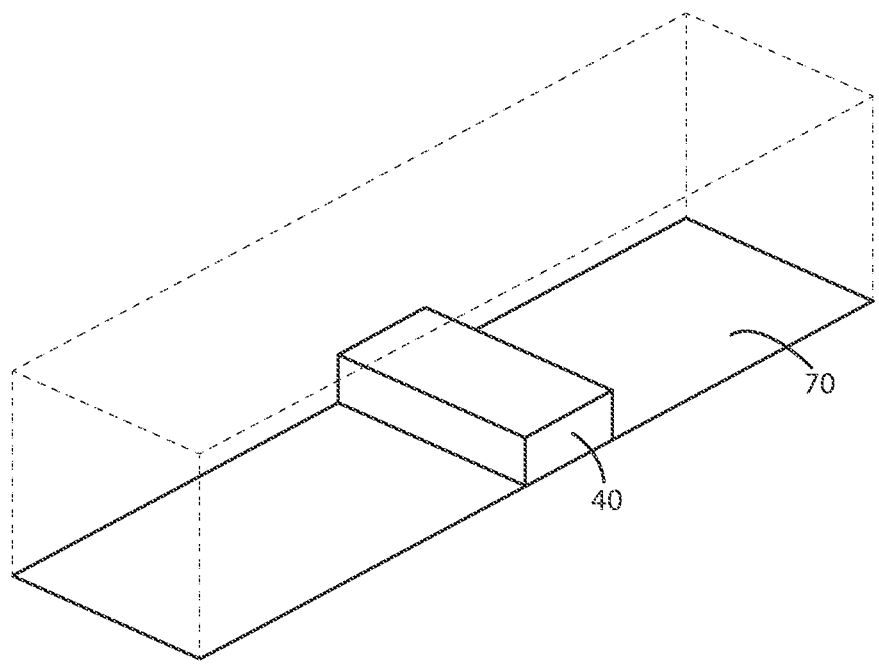
FIG. 18 is an enlarged perspective view of a working electrode in a passageway.

FIG. 18 illustrates a working electrode in a passageway, with it being proud of the surface. A similar configuration could be used in the other analysis chambers, extending across the chamber, or forming a round dot in the center or inserted from the sides as illustrated.

Figure 19:
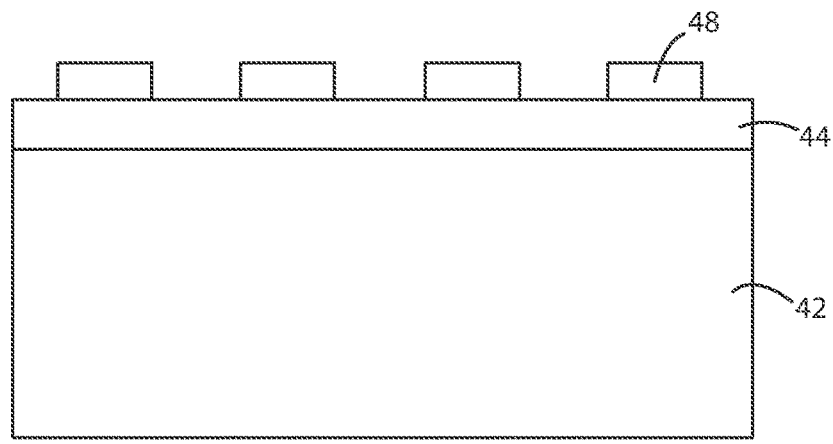
FIG. 19 is a cross sectional of the present invention, including of an exemplary working electrode.
Figure 20:
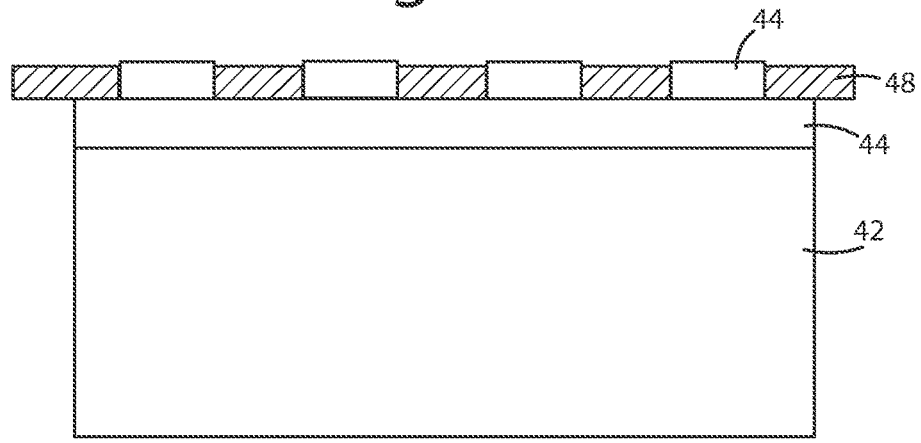
FIG. 20 is a cross sectional of the present invention, including of an exemplary working electrode.
Figure 21:
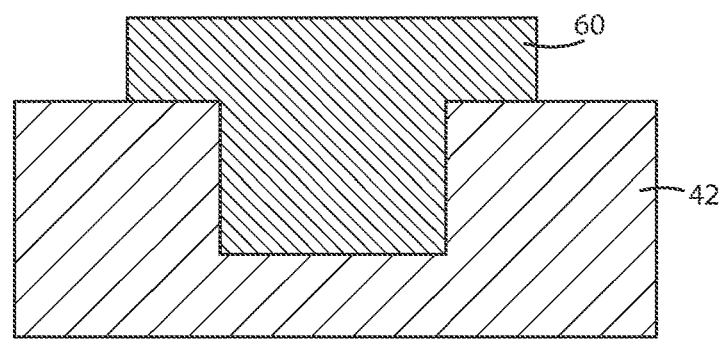
FIG. 21 is a cross sectional of an exemplary counter electrode.

FIG. 19 illustrates a previous method of forming a diamond electrode, which is usable in the present invention, where a thin film of doped diamond 44 is applied to a substrate 42, and then an insulative layer 48 applied over top, and then eroded away to expose the electrode. The above described electrode works well for the method of the present invention, however inventors have developed a new electrode which extends into the chamber or channel, thereby providing a better reading and better interactions with the sample. More specifically, the electrode is proud of the surface or protruding relative to the surrounding surface, instead of being recessed. As illustrated in FIG. 20 a layer of doped diamond, such as boron doped diamond is provided on a substrate. A layer of oxide is then provided on top of the diamond. The oxide is selectively provided or etched away to expose the underlying diamond layer. The oxide if it has no defects, it will not grow diamonds, but also may be treated with a hydrogen plasma to prevent diamond growth. The electrode is then placed in a system to grow diamonds, and the diamonds grow right away on the diamond material, but not the oxide, until they reach a point of being proud to the surface of the oxide. Care must be taken once they are proud to stop the process to prevent the diamond material from growing sideways over the top of the oxide material. In addition to the hydrogen plasma method above, other ways of preheating or changes to the insulating layer may be made to prevent the growth of diamonds. In addition, using the electrode in FIG. 19 as a starting point, chemical preparations could be used, such as sulfuric and nitric acid to erode away the oxide or insulative layer after growing the diamond, such that the diamond is proud to the surface both from growing on top of the existing diamond layer, as well as eroding the insulative layer to provide clean edged electrodes. A counter electrode 60 in cross section is illustrated in FIG. 21.

A schematic diagram of the detector apparatus 10 is illustrated in FIG. 22, and includes a controller 110 and a detector 20. The controller may have various modules, such as the illustrated potentiometer potentiostat 122, pump fluid control 126, cleaning controls 124, and pH control 120. The detector 20 may be any of the above described detectors, but generally will include a working electrode 40, reference electrode 50 and counter electrode 60 in communication with the potentiostat, and optionally a pH electrode 80 and meter 82 in communication with the pH Control 120.

What is claimed is:

1. A method of forming a boron doped diamond electrode comprising the steps of:
   depositing a boron doped diamond material on a substrate;
   adding an insulative material over the boron doped diamond material;
   growing additional boron doped diamond material on an exposed portion of the boron doped diamond material.

2. The method of claim 1 further including the step of eroding away the insulative material before said step of growing.

3. The method of claim 1 further including the step of treating the insulative material to prevent growth of diamond material before said step growing.

4. The method of claim 3 wherein said step of treating includes at least one treatment selected from the group of: treating the insulative material with a hydrogen plasma, acid washing the insulative material, or ensuring a scratch free insulative surface.

5. The method of claim 1 wherein said step of growing occurs without any additional step of eroding the insulative material.

6. The method of claim 1 further including the step of eroding away the insulative material after said step of growing.

7. A method of detecting trace metals in a fluid sample comprising the steps of:
   applying a first predetermined electroplating potential to electroplate a first metal of interest to a working electrode;
   running a reverse scan to release the first metal from the working electrode to quantify the amount of the first metal;
   applying a second predetermined electroplating potential, which is more negative than the first electroplating potential, to electroplate the first metal and a second metal together on the working electrode;
   running a reverse scan on the working electrode to a positive potential to quantify the first metal and the second metal together;
   repeating the steps of applying a potential and running a reverse scan for each additional desired metal to be quantified; and
   using a chip with a plurality of analysis chambers and wherein further including the step of pumping the fluid sample from one of said plurality of analysis chambers to a new chamber including a working electrode, before each step of applying.

8. The method of claim 7 further including the steps of:
   applying a third predetermined electroplating potential, which is more negative than the first and second electroplating potentials, to electroplate the first, second and third metal together on the working electrode;
   running a reverse scan on the working electrode to a positive potential to quantify the first, second and third metal together.

9. The method of claim 7 further including a step of holding a positive potential to condition/clean the working electrode surface before said step of applying a second predetermined electroplating potential.

10. The method of claim 7 wherein said reverse scan is one of LV, SWV, or DPV.

11. The method of claim 7 wherein each of the applying and running steps are done in parallel in different analysis chambers.

* * * * *